United States Patent
Kump et al.

(10) Patent No.: US 7,409,564 B2
(45) Date of Patent: Aug. 5, 2008

(54) DIGITAL RADIOGRAPHY DETECTOR WITH THERMAL AND POWER MANAGEMENT

(76) Inventors: Ken S. Kump, 614 Crestwood Dr., Waukesha, WI (US) 53188; John R. Lamberty, 429 S. Concord Rd., Oconomowoc, WI (US) 53066; Aaron A. Haen, 1286 Chesterwood La., Pewaukee, WI (US) 53072; Paul R. Granfors, 1053 Lily Ave., Sunnyvale, CA (US) 94086; Jason R. Ertel, 2501 Mary Ann Ct., Waukesha, WI (US) 53188; Jibril Odogba, 497 Welsh Rd., Wales, WI (US) 53183; David C. Neumann, 3731 N. 85 St., Milwaukee, WI (US) 53222; Donald F Langler, 4340 Pilgrim Rd., Brookfield, WI (US) 53005; Ping Xue, 1106 Starlight Ln, Cottage Grove, WI (US) 53527; Habib Vafi, 19260 Baythorn Way, Brookfield, WI (US) 53045; Scott W Petrick, N77 W24677 Century Ct., Sussex, WI (US) 53089

( * ) Notice: Subject to any disclaimer, the term of this patent is extended or adjusted under 35 U.S.C. 154(b) by 837 days.

(21) Appl. No.: 10/805,753

(22) Filed: Mar. 22, 2004

(65) Prior Publication Data
US 2005/0206769 A1 Sep. 22, 2005

(51) Int. Cl.
*G06F 1/00* (2006.01)
*G06F 1/32* (2006.01)
*H04N 5/225* (2006.01)

(52) U.S. Cl. .................. 713/300; 713/320; 348/372
(58) Field of Classification Search ............. 713/300, 713/320
See application file for complete search history.

(56) References Cited

U.S. PATENT DOCUMENTS

| | | | | |
|---|---|---|---|---|
| 6,448,561 | B1 * | 9/2002 | Kaifu | 250/370.09 |
| 6,567,125 | B1 * | 5/2003 | Shimizu | 348/297 |
| 7,079,189 | B2 * | 7/2006 | Tsujii et al. | 348/372 |
| 7,239,685 | B2 * | 7/2007 | Petrick et al. | 378/116 |

* cited by examiner

*Primary Examiner*—Suresh K Suryawanshi
(74) *Attorney, Agent, or Firm*—William Baxter; Ellis B. Ramirez; Michael G. Smith

(57) ABSTRACT

Systems and methods are provided for managing power consumption of a medical imaging detector by the use of triggering signals, environmental condition data, and/or determination of a variable time interval triggering event that is unique for each power consumption state. Systems and methods are provided for managing power and temperature of a device, after receiving a request for a function to be performed by the device determining an "on" trigger component, an "off" trigger component, associated circuits for performing the received function, providing power to the associated circuits upon the occurrence of the "on" trigger component, and removing power to the associated circuits upon the occurrence of the "off" trigger component. Further, an instruction is described for determining and displaying a variable time interval that is indicative of a time to change from one state to a desired state.

40 Claims, 10 Drawing Sheets

DIGITAL RADIOGRAPHY DETECTOR WITH THERMAL AND POWER MANAGEMENT

RELATED APPLICATION

This application is related to U.S. application Ser. No. 10/605,828 (Now U.S. Pat. No. 7,239,685) filed Mar. 22, 2004 entitled "System and Method for Reducing Power Consumption in Digital Radiography Detectors."

FIELD OF THE INVENTION

This invention relates generally to portable health care imaging devices more particularly to managing power and temperature of radiographic imaging detectors.

BACKGROUND OF THE INVENTION

Many medical devices serve the portable healthcare and emergency response markets. Examples of these devices are heart-rate monitors, glucometers, electrocardiogram (ECG) monitors, ultrasound imaging devices, and diagnostic medical imaging devices such as digital radiographic detectors. Regardless of the application, these devices must be small in size, lightweight and battery powered to provide the user of the device with optimum mobility and ease of use. However, the requirements necessary to achieve portability result in severe constraints on space, weight and power dissipation causing an increase in the amount of heat energy generated by the components of the medical device. The primary sources of heat are the various integrated circuit components, and rechargeable batteries that power the device when in use or when battery charging takes place. The net result is that the heat contributes to an overall rise in temperature with both application and structural effects on the medical device. Structural effects or excessive heat generated by small portable electronic devices reduces battery life, reduces component life, reduces the reliability of the device, and increases device failure.

In diagnostic medical imaging devices the problem of heat generation is a greater concern due to high power requirements, usage of complex circuitry for optimal performance that is highly sensitive to heat, and patient safety. In particular, while the high power and high circuit density required by the portable battery powered diagnostic medical imaging devices further exacerbate the problem of heat generation, these devices must satisfy certain medical safety requirements regulating the maximum external surface temperature of the device to insure patient safety. Present medical safety requirements regulating temperature mandate that the maximum allowable external surface temperature of a medical device (i.e., the "skin" temperature) not exceed 50 degrees °C. (122 degrees Fahrenheit), thereby ensuring that contact with a patient will not result in patient discomfort or burning. More specifically, there several regulations and rules regarding the temperature of medical devices, such as IEC 60601-1 promulgated by the International Electrotechnical Commission. These regulations are known to the practitioners of the art.

In the case of digital radiographic or digital x-ray, the electronics in the detector generates a significant amount of heat during image acquisition, due to their electrical power consumption, but can be operated at reduced power when no image is being taken. These devices include a source for projecting an x-ray beam toward an object to be analyzed, such as a medical patient. After the beam passes through the patient, an image intensifier converts the radiation into a signal. With solid state digital x-ray detectors, the photodiode detector elements produce electrical signals that correspond to the brightness of the picture element in the x-ray image projected onto the detector. The signals from the detector elements are read out individually and digitized for further image processing, storage and display, typically by a computer. However, to achieve the required image quality, some time is required for electronic signal levels to fully stabilize between the image detector being restored to full power and acquisition of an image. This stabilization time to interfere with the process of acquiring the image is undesirable because the patient may be in an uncomfortable position, required to hold their breath for the image, or other reasons.

To add to the complexity of the problem the imaging performance characteristics of the detector vary with the temperature of the panel and the temperature of the pixel array. For optimum imaging performance, the panel temperature must remain within a range of temperatures. Techniques utilizing higher x-ray power and longer exposures are in demand in order to provide better images. Thus, there is an increasing demand to remove as much heat as possible from the x-ray tube, as quickly as possible, in order to increase the x-ray exposure power and duration before reaching the operational limits of the tube. At full power, the electronics of the detector consume sufficient power and generates sufficient heat to require a thermal management control subsystem to maintain the panel within the optimum imaging temperature range. Previous attempts at developing cooling systems to remove the heat energy from the relatively high-density packaging of radiographic digital image detectors have primarily used thermal convection systems. These systems move large volumes of heat absorbing air or fluid through the radiographic digital image detector to remove the heat energy created by operation of the device. This large volume requires open spaces around the digital radiographic detector. The necessity of these open spaces limits the overall density of the storage devices relative to the volumetric space of the storage system. However, this technique depletes the finite amount of energy especially in a portable device.

For the reasons stated above, and for other reasons stated below which will become apparent to those skilled in the art upon reading and understanding the present specification, there is a need in the art for a reliable, simple and efficient manner to provide a thermal management system in a portable battery powered electronic device, and particularly, in a portable battery powered diagnostic medical imaging device, which addresses the foregoing problems. There is also a need for improved management of power consumption in portable devices such as digital radiographic detector to increase power conservation and increase efficiency.

SUMMARY OF THE INVENTION

The above-mentioned shortcomings, disadvantages and problems are addressed herein, which will be understood by reading and studying the following specification.

The present technique provide for a method of regulating the operation of a digital radiography detector by detecting a first triggering signal, acquiring environmental condition data from the digital radiography detector, changing operating state of digital radiography detector based on the detected first triggering signal, determining a variable time interval triggering event signal from the changed operating state of the digital radiography detector and acquired environmental condition data. Further, the technique upon detecting a second triggering signal automatically changes the operating state of the digital radiography detector at the occurrence of either a second triggering event or determined variable time interval triggering event. The type of environmental condition data includes battery status, battery capacity, error status, internal temperature, ambient temperature, operating state, and diagnostic data.

Another embodiment of the invention is to a computer-accessible medium having executable instructions for regulating the operation of the digital radiography detector to an off state, standby state, and an on state. The executable instructions capable of directing a processor to perform detecting a first triggering signal, acquiring environmental condition data from digital radiography detector, changing operating state of digital radiography detector based on the detected first triggering signal, determining a variable time interval from the changed operating state of digital radiography detector and acquired environmental condition data, detecting a second triggering signal, changing operating state of digital radiography detector at the occurrence of either one of a second triggering signal and determined variable time interval triggering event.

Another embodiment is to an apparatus for regulating the operation of a digital radiography system using a receiver of a first triggering signal, device for acquiring environmental condition data from digital radiography detector, a device for changing operating state of digital radiography detector based on the detected first triggering event; a determiner of a variable time interval triggering event from changed operating state of digital radiography detector and acquired environmental condition data. A receiver of a second triggering event and a device for changing operating state of digital radiography detector at the occurrence of either one of a second triggering signal and determined variable time interval triggering event.

Another aspect of the invention is to a method and apparatus for managing the power and temperature of a device receiving a request for a function to be performed by the device, determining from the received request for a function to be performed by the device an on trigger component, an off trigger component, associated circuits for performing the received function, providing power to the associated circuits upon the occurrence of the on trigger component, removing power to the associated circuits upon the occurrence of the off trigger component.

Yet another embodiment is to a computer data signal embodied in a digital data stream comprising data including a representation of instructions for managing the power and temperature of a device, wherein the computer data signal is generated by a method of receiving a request for a function to be performed by the device, determining from the received request for a function to be performed by the device an on trigger component, an off trigger component, associated circuits for performing the received function. The data signal then provides power to the associated circuits upon the occurrence of the on trigger component, removes power to the associated circuits upon the occurrence of the off trigger component. The device is a digital radiography detector and the function requested can be selected from a number of functions such as "integrate x-ray signal," "read pixel array," "scrub pixel array," "read sensors," and "perform diagnostics." Further, the on trigger component can be selected from x-ray prep switch, compression paddle motion, command from system, timeout fixed time without activity, command from system, activation switch, and reset switch and the off trigger component can be selected from end of readout of x-ray frame, end of readout of offset frame, fixed time without any activity timeout, end of readout, end of reading sensors, end of transmitting data, diagnostic tests complete, diagnostic test data transferred. Finally, the associated circuits can be selected from panel bias, scan row enable, data column enable, transmit, receive, optical power sense, control circuitry, sensor circuitry.

Another aspect of the invention is an apparatus and method to manage power consumption of a medical imaging detector by receiving a first triggering signal, changing the medical imaging detector to a first power consumption state based on the received first triggering signal, receiving a second triggering signal; and changing the medical imaging detector to a second power consumption state based on the received second triggering signal. In some embodiments, the predictor signal is derived from a prediction model. The prediction model is based on one or more correlation of pressure data, correlation of force data, probability prediction based time and force of activation, statistic based on prior use, patient identifier indicia reader.

Another embodiment of the invention is a computer-accessible medium having executable instructions to perform indicating state information for a medical imaging system, the executable instructions capable of directing a processor to acquiring state information of a medical imaging detector, displaying the acquired state information of the medical imaging detector and determining if the acquired state information matches reference state information of the medical imaging detector. If there is a match, the operation of the medical imaging detector changed based on the determination of the acquired state and the reference state information. If the comparison of the acquired state information and reference state information do not result in a match, then the state of the medical imaging detector is changed upon the occurrence of a triggering signal. The change of the state of the detector, the instruction determines a variable time interval that is indicative of the estimated time to change from the acquired state to the triggered state and displaying interval that is indicative of the estimated time to change from the acquired state to the triggered state.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Overview

Figure 1:
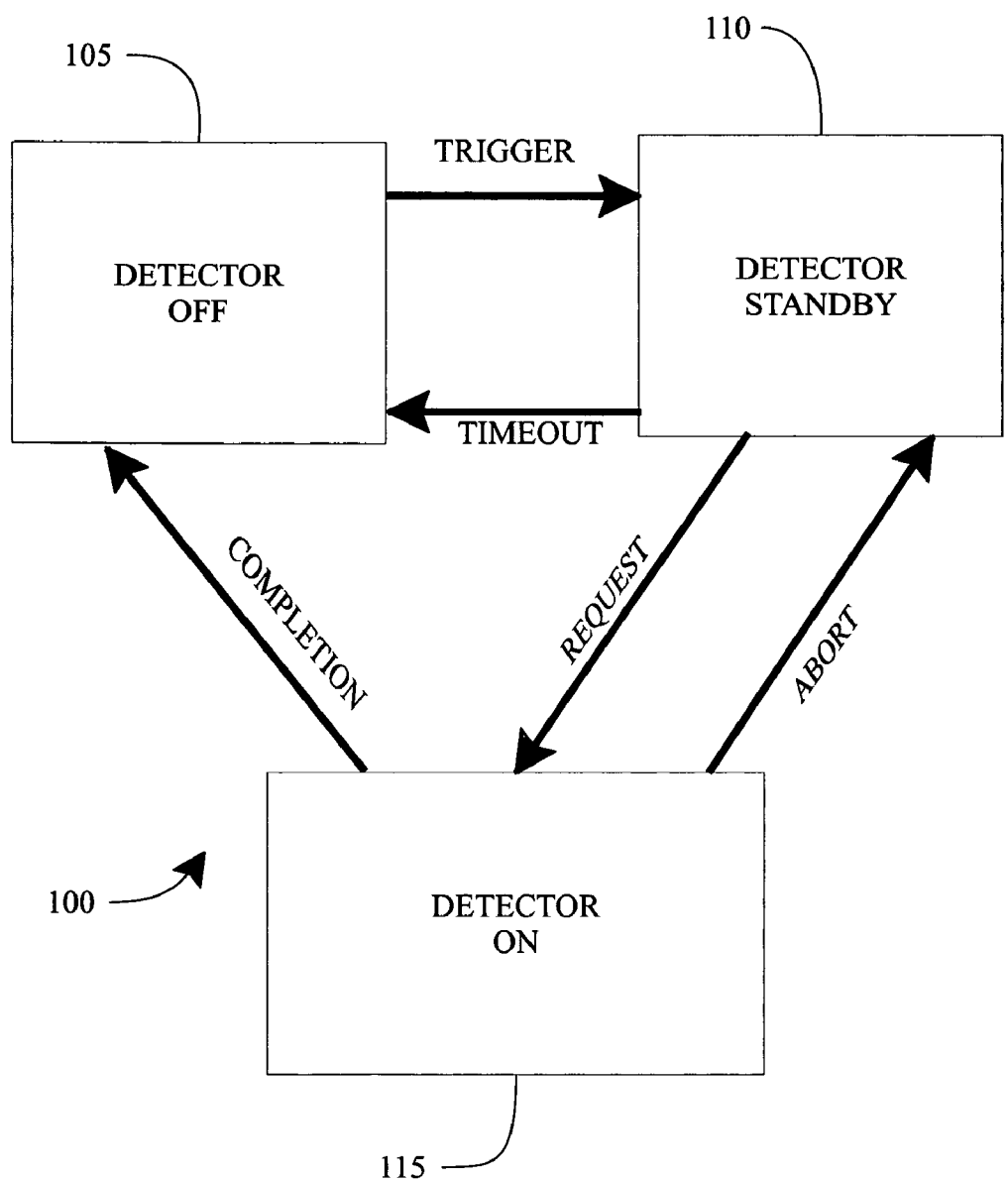
FIG. 1 is a diagram depicting operating modes of the radiographic detector.

FIG. 1 is an overview of a representation of power consumption states 100 in a device such as an image detector, according to an embodiment. Operating states include an "OFF" state, a "Standby" state and an "ON" state. These states are selected to achieve maximum power conservation and optimal temperature management.

In OFF state 105, limited or no power is applied to the device. In this state, only the essential components are supplied with power. Examples of such essential components are controllers and a display in the device.

In standby state 110, marginal power is applied to the device. In standby state 110, the device awaits authorization to initiate or fulfill an image acquisition. Standby state 110 can also be called the idle state or ready state where all components necessary to make an x-ray image are powered on and stabilized so that x-ray imaging is possible.

In ON state 115, full power is applied to the device, such as when the device receives an image acquisition request. Once the system trigger is activated, the ON state 115 is used as a signal by the device's controller or imaging device controller to wake up the device from a sleep mode/device off state 105 to a ready mode/device standby state 110 and may await a secondary trigger to transition to a full-power mode/device on state/ready state 115 to signify the beginning of x-ray exposure request.

The device is programmed with a unique timeout for each mode to automatically transition into another lower power mode, if the expected system trigger does not occur within the allotted time. For example, upon the receipt of the beginning of an exposure request before the time out expires, the device shall transition from a ready mode to an imaging mode/device on state 115 and perform the image acquisition.

After successfully completing an image acquisition, if no further image requests are received within a specified (timeout) period or based on another inherent system activity, the device will be put in a sleep mode/device off state 105 until a system trigger initiates another image request. In the event that the beginning of an image request is terminated, aborted, scrapped the device will revert to the standby mode because it is assumed that an image acquisition will be requested in the near future. The various timeouts can be configured uniquely for each customer instance to customize the performance and meet the patient workflow requirements. In addition, the controller may adapt its timeouts based on the battery capacity or battery status to conserve additional power or adapt to the different ambient environmental conditions of the room.

The selective application of power to the device enables reduced-power operation of the device at times when no image acquisition is imminent. Selective application of power reduces heat generation in the image device, thus reducing the amount of cooling apparatus needed to remove heat from the device, or reduce the amount of work the cooling apparatus needs to maintain the device below the maximum allowed temperature. Additionally, by reducing heat generation, the mean-time-to-failure of the electronic components in the device will be extended. Similarly, by reducing the workload on the cooling apparatus of the device, the mean-time-to-failure of such cooling apparatus will also be extended. By reducing either the amount or size of the cooling apparatus or the amount of work such cooling apparatus must perform to maintain the device below the maximum allowed temperature, undesirable aspects of the cooling apparatus will be reduced, including cooling fan noise, volumetric flow and temperature of air moved by the cooling fan, and the overall mass and volume of the portable device itself, which are both desired to be as small as possible for the image area coverage required.

Apparatus

Figure 2:
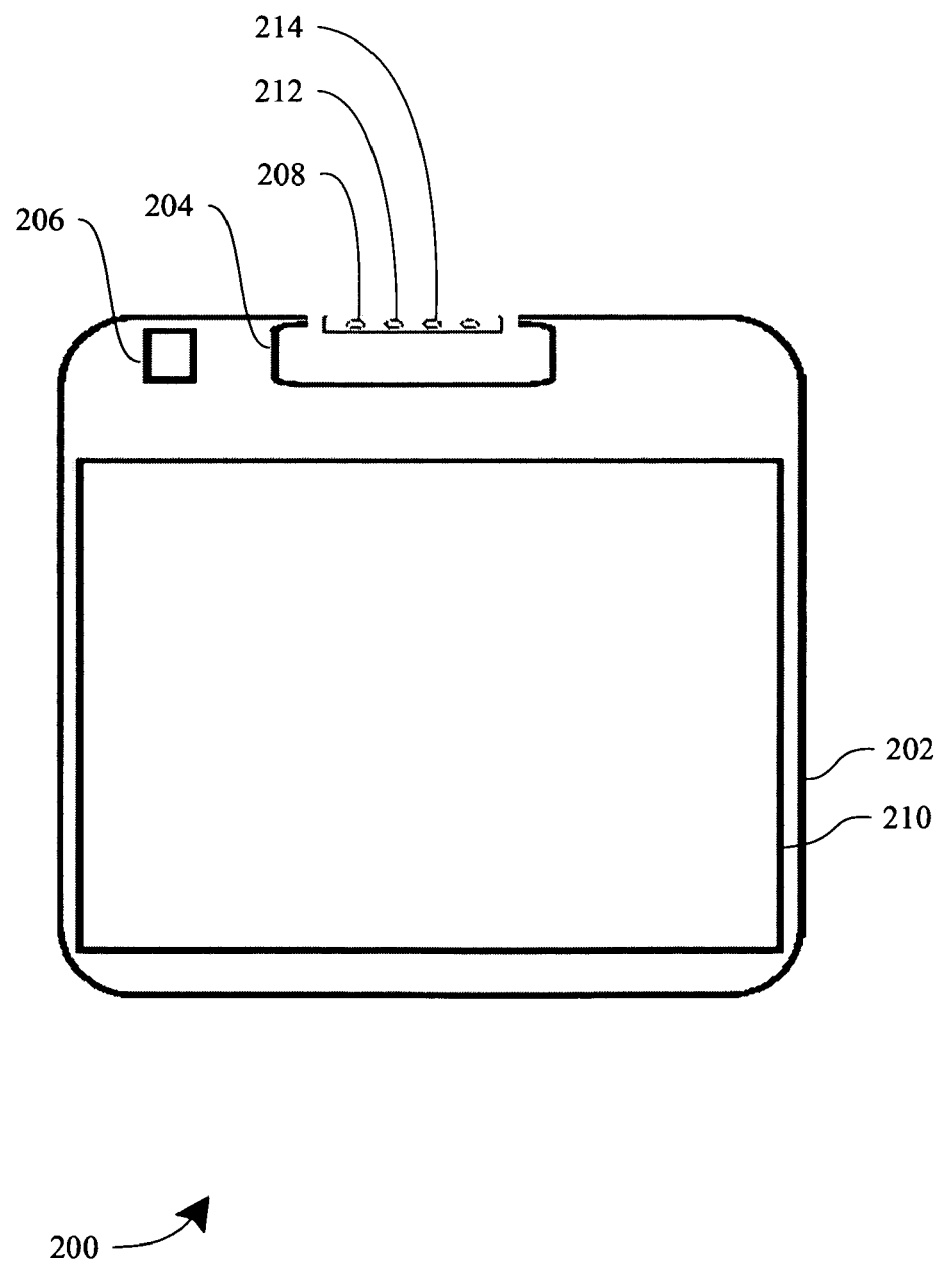
FIG. 2 is a diagram illustrating a radiographic imaging detector.

FIG. 2 is an exemplary digital radiography detector system 200 of an embodiment of the invention. The digital radiography detector system 200 includes a protective case 202, a handle 204, an indicator 206, a sensor unit or activation switch 208, a digital radiography detector 210, and patient indicia reader 212 and reset switch 214. The digital radiography detector system 200 may be coupled to a positioning system for movement to a desired orientation relative to a patient or object to be inspected.

Figure 3:
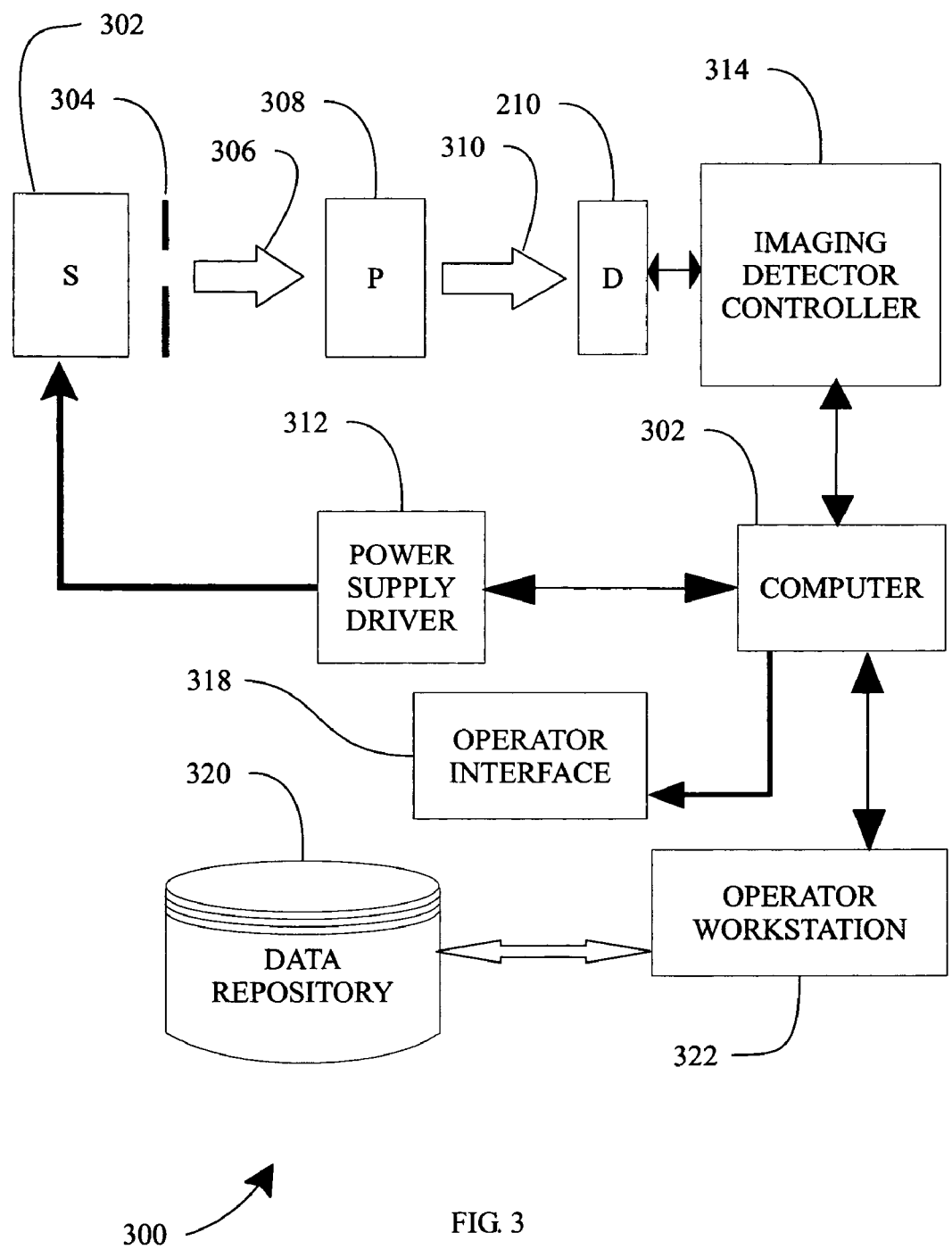
FIG. 3 is a diagram illustrating an overview of a radiographic imaging system in which the present technique may be utilized.
Figure 5:
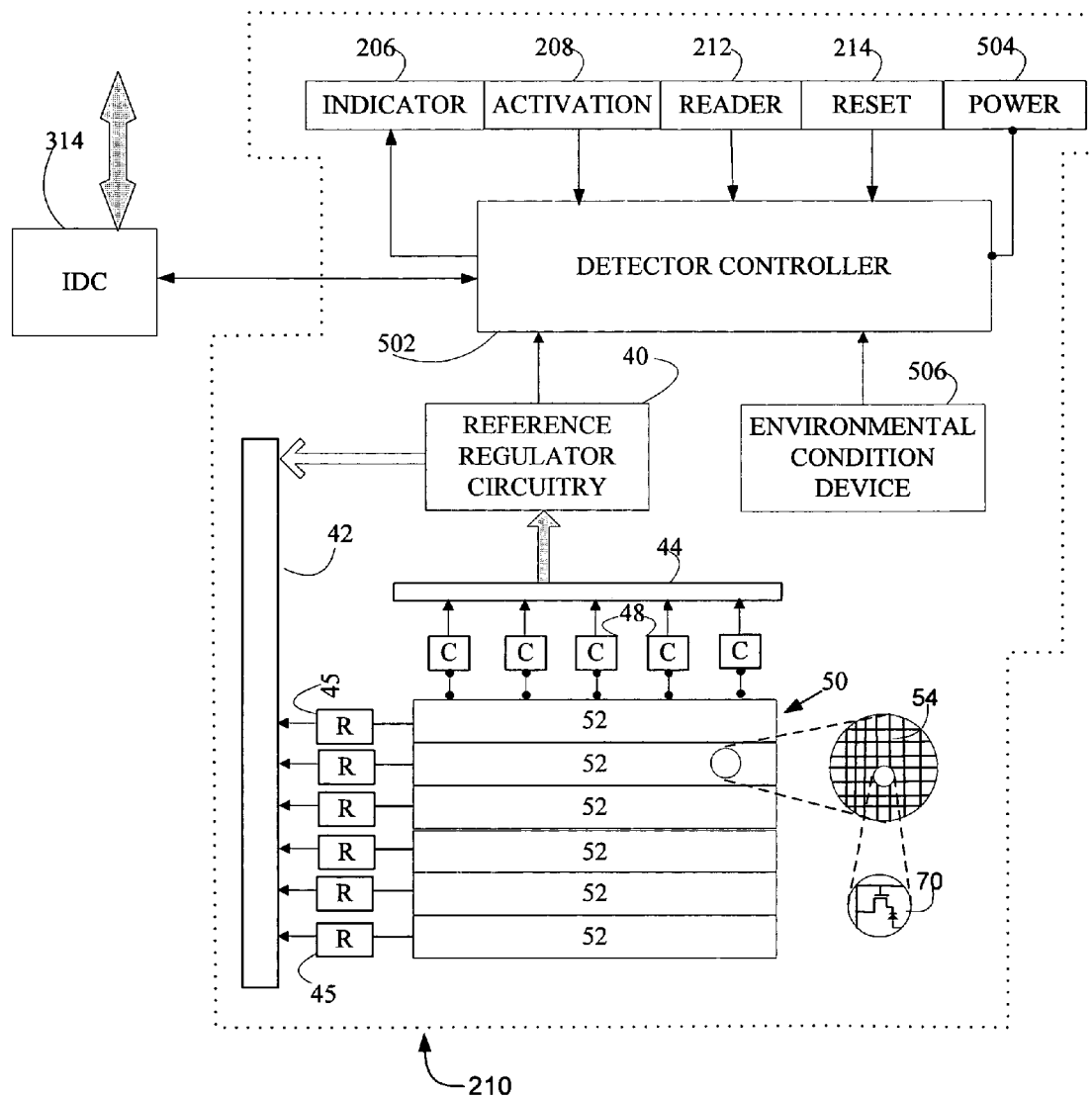
FIG. 5 is a block diagram of the hardware and operating environment of the radiographic detector.
Figure 6:
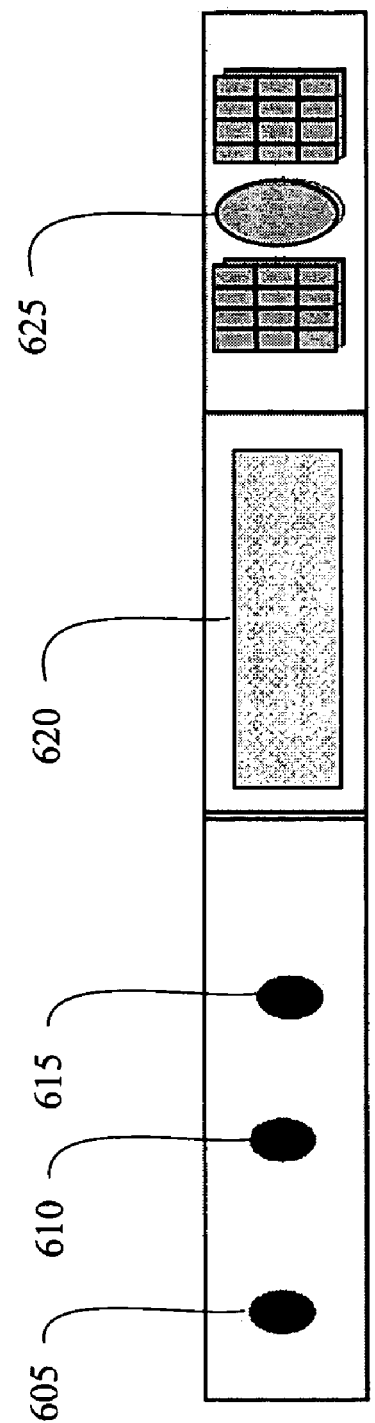
FIG. 6 is a diagram illustrating an indicator that the present technique may utilize.

The indicator 206 may be coupled to detector controller, such as imaging detector controller 314 in FIG. 3, or computer 316 in FIG. 3 through a detector controller 502 in FIG. 5. In some embodiments, the indicator 206 can be one or more light emitting diode, liquid crystal display, tactile indicator such as vibration, voice generation or any other know or later developed display devices for conveying information. The information is an indication to the user or operator of the state, function, or operation of the detector. FIG. 6 describes information that might be useful to the operator of detector 210.

The activation switch 208 for sensing a change in operator interaction with detector 210 may be coupled to detector controller 502 in FIG. 5 or computer 316 in FIG. 3. The activation switch 208 can be one or more electrical, optical, capacitive or any known or later developed activation switch for signaling a change in user or operator interaction. When an operator or user grabs the handle 204 of the digital radiography detector system 200, a signal is emitted and processed by either the detector controller 502 or computer 316 as a triggering signal or triggering event. The triggering signal can be set by software or hardware to indicate interaction with the system. The trigger can be as sensitive as a touch of the activation switch or as robust as a firm grip on handle 204. Thus, the triggering event or signal point can be set at a level ranging from zero to one hundred percent of a desired voltage level or duty cycle. The activation switch 208 can be positioned along the entire part of the handle. It should be understood that other possible handles could be used for manipulating the position of the system without departing from the spirit of the invention and functionality of the activation switch 208. By positioning the activation switch on the radiography detector system 200 the electronics of the device can start the stabilization process much faster since the operator need not be at the station.

FIG. 3 illustrates diagrammatically a medical imaging system 300 for acquiring and processing discrete pixel image data. For illustration purposes, medical imaging system 300 is a digital X-ray system designed both to acquire original image data and to process the image data for display in accordance with the present technique. In the embodiment illustrated in FIG. 3, medical imaging system 300 includes an X-ray radiation source 302 positioned adjacent to a collimator 304. Collimator 304 permits a stream of radiation 306 to pass into a region in which a subject 308, such as a human patient, is positioned. A portion of the radiation 310 passes through or around the subject 308 and impacts a digital X-ray detector 210. The detector 210 converts the X-ray photons received on its surface to lower energy photons, and subsequently to electric signals, which are acquired and processed to reconstruct an image of the features within the subject.

Source 302 is controlled by a power driver circuit 312, which furnishes both power, and control signals for examination sequences. Moreover, detector 210 is coupled to an imaging detector controller 314, which commands acquisition of the signals generated in the detector 210. Detector controller 314 may also execute various signal processing and filtration functions, such as initial adjustment of dynamic ranges, interleaving of digital image data, and so forth. Both power driver circuit 312 and detector controller 314 are responsive to signals from a computer 316. In general, computer 316 commands operation of the medical imaging system 300 to execute examination protocols and to process acquired image data. In the present context, computer 316 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 3, computer 316 is linked to at least one operator interface device 318 such as a display or a printer. The operator interface 318 may include standard or special purpose computer monitors and associated processing circuitry. System 300 also includes one or more data repositories 320 for downloading patterns of use or statistical analysis of prior behavior so as to efficiently operate the detector 210, and assigning a unique identifier for one or more patient, image, or session that can be affixed to the image produced by detector 210.

The data in the repository 320 can be used to derive prediction models for determining unique triggering events for the operator and detector 210. The prediction models can be statistical, regression, or pattern recognition based like a neural network. The continuous measurement of pressure or force on the handle activation switch 208 over time, sampled about once per second or more frequently, may be used to statistically predict when an image is likely to be taken in the near future. The result is a time-varying pattern of pressure or force on the handle switch versus image acquisition being desired within a certain period. A statistical model can be assembled from correlations of pressure or force data over time versus when image acquisition is desired, other predictors or models could be based on a data set determined by clinical studies, or could be based on a data set accumulated for that particular detector or system, or based on a data set accumulated from a collection of detectors or systems all in use in a particular facility, such as the radiology department of a specific hospital or clinic.

Further, the same statistical data can be used for determining when to switch to different operating modes, detector idle state or detector on state, as enumerated with reference to FIG. 1. When individual detectors 210 perform continuous or periodic updating of the statistics and such information is combined in data repository 320 it is then possible to predict when an image acquisition was likely to be desired from an image detector based on the work patterns, exam patterns, and habits and practices of workers at that hospital or clinic. Another prediction model that can be derived is a neural network such as a back-propagation network for finding patterns of detector activation given an input layer and an output layer.

One or more operator workstations 322 may be further linked in the system for outputting system parameters, requesting examinations, viewing images, downloading data such as patterns and statistics of use for operating the detector 210 and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth. The interconnection of workstations throughout hospital facilities, geographical locations, or flexibly defined groups enhances predictor quality due to an increase in observation.

Figure 4:
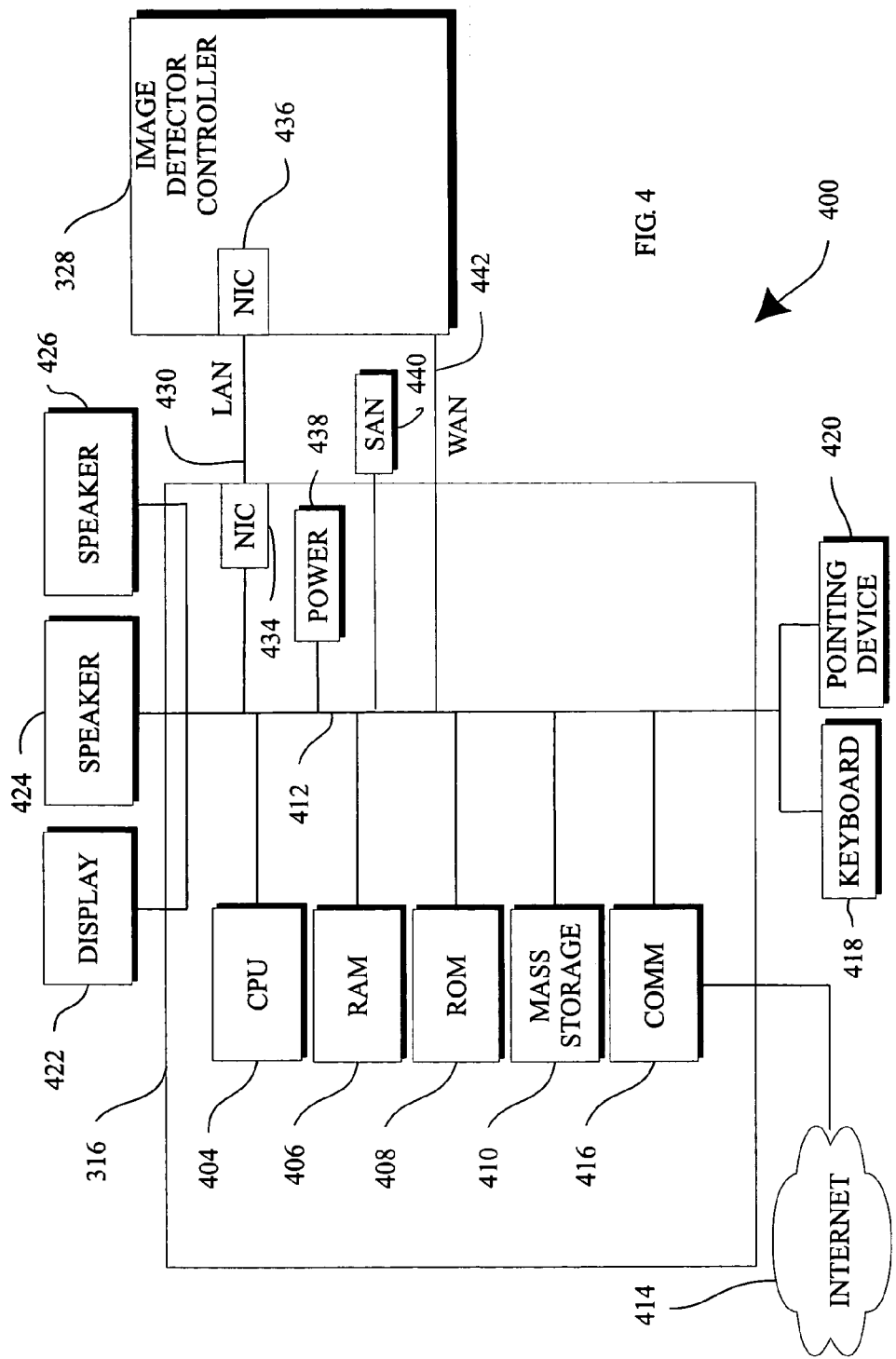
FIG. 4 is a block diagram of the hardware and operating environment in which different embodiments can be practiced.

FIG. 4 is a block diagram of the hardware and operating environment 400 in which different embodiments can be practiced. The description of FIG. 4 provides an overview of computer hardware and a suitable computing environment in conjunction with which some embodiments can be implemented. Embodiments are described in terms of a computer performing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 316 includes a processor 404, commercially available from Intel, Motorola, Cyrix and others. Computer 316 also includes random-access memory (RAM) 406, read-only memory (ROM) 408, and one or more mass storage devices 410, and a system bus 412, that operatively couples various system components to the processing unit 404. The memory 406 and 408, and mass storage devices, 410, are types of computer-accessible media. Mass storage devices 410 are more specifically types of nonvolatile computer-accessible media and can include one or more hard disk drives, floppy disk drives, optical disk drives, and tape cartridge drives. The processor 404 executes computer programs stored on the computer-accessible media.

Computer 316 can be communicatively connected to the Internet 414 via a communication device 416. In one embodiment, the communication device 416 is a modem that responds to communication drivers to connect to the Internet via what is known in the art as a "dial-up connection." In another embodiment, a communication device 416 is an Ethernet® or similar hardware network card connected to a local-area network (LAN) that itself is connected to the Internet via what is known in the art as a "direct connection" (e.g., T1 line, etc.).

A user enters commands and information into the computer 316 through input devices such as a keyboard 418 or a pointing device 420. The keyboard 418 permits entry of textual information into computer 316, as known within the art, and embodiments are not limited to any particular type of keyboard. Pointing device 420 permits the control of the screen pointer provided by a graphical user interface (GUI) of operating systems such as versions of Microsoft Windows®. Embodiments are not limited to any particular pointing device 420. Such pointing devices include mice, touch pads, trackballs, remote controls and point sticks. Other input devices (not shown) can include a microphone, joystick, game pad, satellite dish, scanner, or the like.

In some embodiments, computer 316 is operatively coupled to a display device 422. Display device 422 is connected to the system bus 412. Display device 422 permits the visual display of information, including computer, video and other information, for viewing by a user of the computer. Embodiments are not limited to any particular display device 422. Such display devices include cathode ray tube (CRT) displays (monitors), as well as flat panel displays such as liquid crystal displays (LCD's). In addition to a monitor, computers typically include other peripheral input/output devices such as printers (not shown). Speakers 424 and 426 provide audio output of signals. Speakers 424 and 426 are also connected to the system bus 412.

Computer 316 also includes an operating system (not shown) that is stored on the computer-accessible media RAM 406, ROM 408, and mass storage device 410, and is and executed by the processor 404. Examples of operating systems include Microsoft Windows®, Apple MacOS®, Linux®, UNIX®. Examples are not limited to any particular operating system, however, and the construction and use of such operating systems are well known within the art.

Embodiments of computer 316 are not limited to any type of computer 316. In varying embodiments, computer 316 comprises a PC-compatible computer, a MacOS®-compatible computer, a Linux®-compatible computer, or a UNIX®-compatible computer. The construction and operation of such computers are well known within the art.

Computer 316 can be operated using at least one operating system to provide a graphical user interface (GUI) including a user-controllable pointer. Computer 316 can have at least one web browser application program executing within at least one operating system, to permit users of computer 316 to access intranet or Internet world-wide-web pages as addressed by Universal Resource Locator (URL) addresses. Examples of browser application programs include Netscape Navigator® and Microsoft Internet Explorer®.

The computer 316 can operate in a networked environment using logical connections to one or more remote computers, such as imaging detector controller 314. These logical connections are achieved by a communication device coupled to, or a part of, the computer 316. Embodiments are not limited to a particular type of communications device. The detector controller 314 can be another computer, a server, a router, a network PC, a client, a peer device or other common network node. The logical connections depicted in FIG. 4 include a local-area network (LAN) 430 and/or a wide-area network (WAN) 432. Such networking environments are commonplace in offices, enterprise-wide computer networks, intranets and the Internet.

When used in a LAN-networking environment, the computer 316 and imaging detector controller 314 are connected to the local network 430 through network interface or adapter 434, which is one type of communications device 416. Remote computer or imaging detector controller 314 also includes a network device 436. When used in a conventional WAN-networking environment, the computer 316 and detector controller 314 communicate with WAN 432 through modems (not shown). The modem, which can be internal or external, is connected to the system bus 412. In a networked environment, program modules depicted relative to the computer 316, or portions thereof, can be stored in the detector controller 314.

Computer 316 also includes power supply 438. Each power supply can be a battery. In some embodiments, computer 316 is also operably coupled to a storage area network device (SAN) 440 which is a high-speed network that connects multiple storage devices so that the multiple storage devices may be accessed on all servers in a LAN such as LAN 430 or a WAN such as WAN 432. This arrangement permits multiple sources for predictive models, multiple sources for statistical analysis, and the sharing of information so as to efficiently and automatically manage power and heat generation by the radiography imaging detector 200.

FIG. 5 is a block diagram that illustrates detector 210. Embodiments are described as operating in a multi-processing, multi-threaded operating environment on a computer, such as computer 316 in FIG. 3 and FIG. 4. FIG. 5 is a diagrammatical representation of functional components of digital detector 210.

FIG. 5 includes an imaging detector controller (IDC) 314, which in some embodiments will be configured within a detector controller 502. IDC 314 includes a CPU or digital signal processor as described in FIG. 4, as well as memory circuits for commanding acquisition of sensed signals from the detector 210. In some embodiments, IDC 314 is coupled via two-way fiberoptic conductors to detector control circuitry 502 within detector 210. IDC 314 thereby exchanges command signals for image data within the detector during operation.

Detector controller 502 circuitry receives DC power from a power source, represented generally at reference numeral 504. Detector controller 502 is configured to originate timing and control commands for row and column drivers used to transmit signals during data acquisition phases of operation of the system. Detector controller 502 therefore transmits power and control signals to reference/regulator circuitry 40, and receives digital image pixel data from circuitry 40. Additionally indicator 206, activation switch 208, reader 212 such as a bar code reader, reset switch, and environmental condition device 506 are coupled to detector controller. The detector can be equipped with a bar code reader 212 for reading a unique identifier for either the patient or the operator of the device.

The controllers can use this action of reading the unique identifier as a trigger to switch between modes. The purpose of the activation switch 208 is to use the status of the switch in conjunction with historical or generally statistical data to infer whether the state of the detector is likely to change. The purpose of the indicator 206 is to convey to the user or operator the status of the detector. The environmental condition device 506 monitors the detector battery status, detector error status, temperatures of other devices or room, diagnostics, internal temperature, voltage or state of the panel/detector can be attained in this manner. That is, the detector 210 may be commanded or contains internal control to transition between modes without a system trigger. In so doing, the internal detector temperature can be maintained by going between the modes of operation. This requires a feedback loop either internal to the detector or remote to the imaging detector controller 314, computer 316, or workstation 322. In addition, a background process exists to periodically transition the detector between modes to assess information from the detector. That is, the detector could be interrogated by computer 316 or any other external device to read the content of the environmental condition device 506 and then use the retrieved data as a condition for change between the modes of operation.

combines the LEDs, display, and audio indicators. Other combinations are possible without departing from the scope of the embodiment. Table I illustrates possible relationships between the status and indicator:

TABLE I

| STATUS | LED1 Duty Cycle | LED2 Duty Cycle | LED3 Duty Cycle | INDICATOR | AUDIO |
|---|---|---|---|---|---|
| Detector Off State | off | off | off | Off | Off |
| Sleep or idle mode | half | off | off | Sleep | Off |
| Detector ON or Ready | one | off | off | On | Off |
| Image Transfer | third | off | off | Imaging | Off |
| Temperature Exceeded | off | one | off | Temp | LNG Blip |
| BIST error | off | one | off | Error(BIST) | Off |
| Power Timeout | off | half | off | TMOUT | series of Blips |
| Wait for offset acquisition | third | off | off | ACQ | Off |
| Temperature Warning | off | off | one | TWRN | Off |
| Battery charging | off | off | third | CHRGING | Off |
| Battery low | off | off | one | LOW | Off |
| Battery done charging | off | off | blink | High | Short Blip |
| Battery too low for operation | off | blink | off | Charge | Off |
| LED functioning | one | one | off | LED Pass | Off |
| Diagnostic Test running | half | half | off | D Test | Off |
| Diagnostic PASS | one | off | off | D Pass | Off |
| Diagnostic FAIL | off | third | off | D Fail | Off |
| Diagnostic Test in Process | off | off | Half | DGNST | Off |

In a present embodiment, detector 210 consists of a scintillator that converts X-ray photons received on the detector surface during examinations to lower energy (light) photons. An array of photodetectors then converts the light photons to electrical signals, which are representative of the number of photons or the intensity of radiation influencing individual pixel regions of the detector surface. Readout electronics convert the resulting analog signals to digital values that can be processed, stored, and displayed, such as in a operator interface 318 or a workstation 322 following reconstruction of the image. In the particular embodiment illustrated in FIG. 5, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector. As also illustrated in FIG. 5, each pixel 54 is generally defined at a row and column crossing, at which a column electrode 48 crosses a row electrode 45 as shown in item 70.

FIG. 6 is an illustration of the indicator 206 for conveying information to the operator or user of the digital radiographic detector 210. The indicator may consist of one or more light emitting diodes (LEDs), alphanumeric display, or an audio indicator that can generate voice or any other audible sound. The indicator 206 illustrated in FIG. 6 has green LED 605, red LED 610, amber LED 615, alphanumeric display 620, and a speaker 625. In combination these indicators can inform the operator of the state of the detector 210, the time that is required to shift between states, diagnostic conditions, and temperature and environmental conditions. The following table, while not comprehensive of the different permutations, The detector state indicator 206 provides the user with the state of the detector and approximately how much time is required to complete a transition between states. The arrangement of the indicator 206 allows for information that may be available at the computer 316 or workstation 322 to also be available at the detector 210 for a quick assessment of detector operating status.

The system level overview of the operation of an embodiment has been described in this section of the detailed description. While the system 400 is not limited to any particular controller or computer, for sake of clarity a simplified computer or controller has been described.

Methods

In the previous section, a system level overview of the operation of an embodiment was described. In this section, the particular methods performed by processors such as processor 404 are described by reference to a series of flowcharts. Describing the methods by reference to a flowchart enables one skilled in the art to develop such programs, firmware, or hardware, including such instructions to carry out the methods on suitable processors. Similarly, the methods performed by the server computer programs, firmware, or hardware are also composed of computer-executable instructions. Methods 700, 800, 900, and 1000 are performed by programs executing on, or performed by firmware or hardware that is a part of, a computer, such as computer 316 in FIG. 3, and is inclusive of the acts required to be taken by detector 210 and image detector controller 314. In this way the operator need not worry about cycling the radiography imaging detector 200 through the different power states, the system automatically manages power consumption and heat generation.

Figure 7:
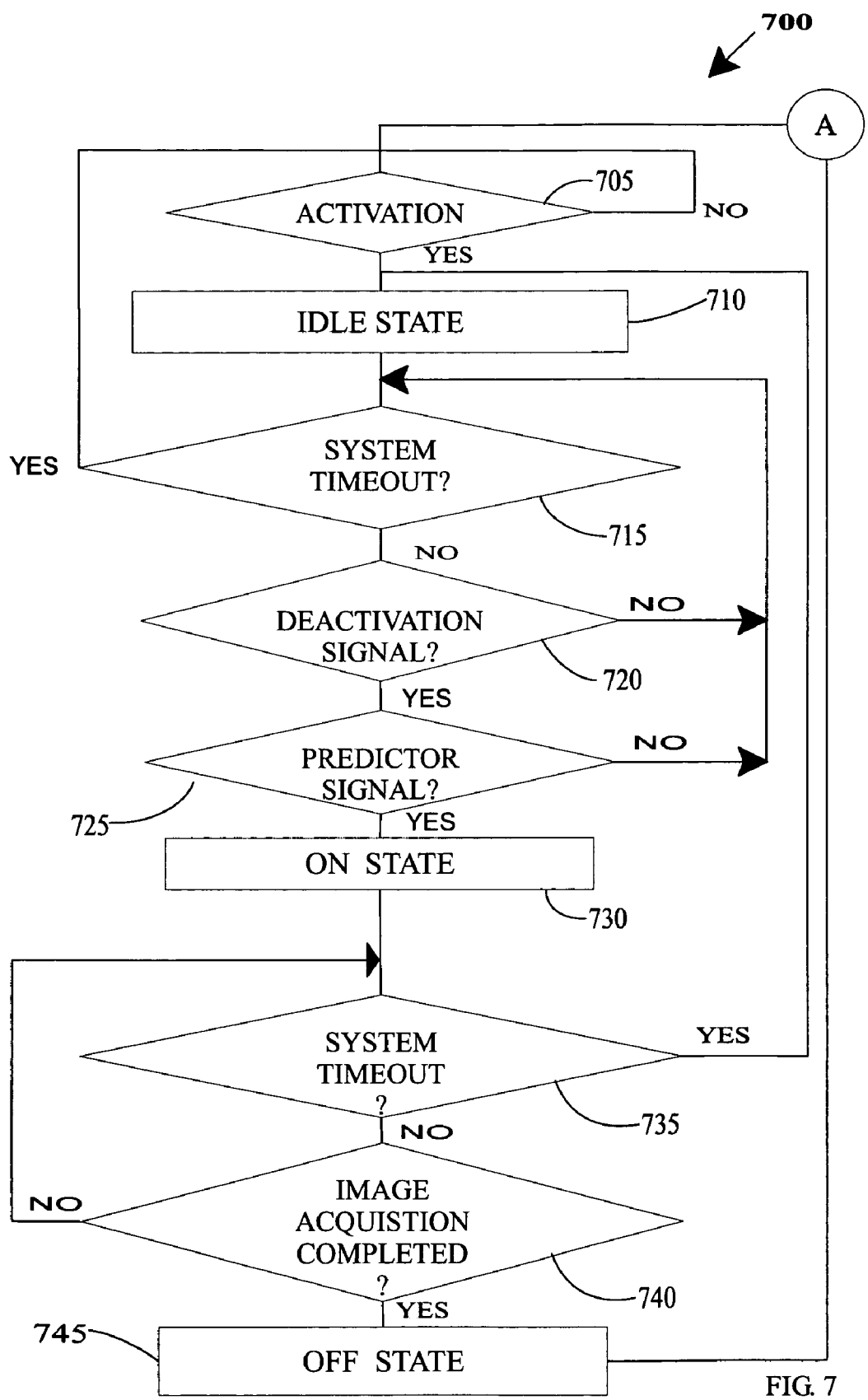
FIG. 7 is a flowchart of a method performed according to an embodiment showing predictor model and system timeout.

FIG. 7 is a flowchart of a method 700 performed by either computer 316, imaging detector controller 314, detector controller 502, operator workstation 322, or by a selective combination of the above according to an embodiment. Method 700 satisfies the need in the art for a reliable, simple and efficient manner to provide a thermal management system with increased power conservation and increased efficiency in a portable battery powered electronic device, and in particular, in a portable battery powered diagnostic medical imaging device.

FIG. 7 is a flowchart of an exemplary method 700 for temperature and power management according to an invention. In action 705, an activation signal is determined to begin the process. This activation can be the status of activation switch 208 or a system cue from any of the system, detector, imaging detector, work station controller. The status of the activation switch 208 may include a signal that is indicative of activation, pressure, change in capacitance, change in induction, change in an electrical parameter, a system cue or any other form of information that is indicative of an actuation of activation switch 208. This signal is treated as a trigger by the detector controller 502, imaging detector controller 314, computer 316, or operator workstation 322 so as to initiate power or thermal management. If the determination is that activation has not occur the process returns to the beginning. If a determination is made that activation has occur then the process continues to action 710.

In action 710, the detector is placed in the detector standby state 110 or idle state. Initially in the standby state or idle state, no image will be taken while the operator or technician is holding the detector resulting in a minimum amount of heat and battery depletion. The process continues to action 715.

In action 715, a system timeout is determined. The system timeout could be a count, a timestamp which signals when the detector was placed in the idle state, a delta that is the difference between an average time based on prior performance and the current time, or an automatic count down process based on a statistical model. If a timeout event occurs then the detector 210 is put into a detector off state to manage the depletion of the power source and to insure proper temperature range so as to not cause performance degradation or patient injury. If action 715 is within a safe harbor or a timeout trigger has not been initiated then the process continues to action 720.

In action 720, a deactivation is determined the deactivation is the mirror image of the activation of action 705. When the operator releases the switch on the handle it is an indication that the operator has finished positioning the image detector 210 and presumably is ready to take an image. Because this release is a precursor action to taking an image, reception of this transition of the switch state indicates to the system that the image detector should be changed from the standby or idle state to imaging state. The process monitors the deactivation of the switch and loops until either the switch is deactivated or a timeout condition has occurred in action 715. Once the deactivation condition has been met, control passes to action 725.

In action 725, a predictor model is consulted. The predictor model tries to ascertain or predict what consequences or results are most likely to follow from the release of the switch. The predictor can be program or device that supports spreadsheet functions, scenario planning, simulation, or any other application that can be used to predict future outputs based on a well-tailored set of conditions. The conditions can be system cues, such as the technician activating the X-Ray tube prep switch, the technician adjusting X-Ray technique parameters or other system controls, or lack of such activity, to determine if the image detector should proceed to the imaging state or the detector on state. Yet, other system cues can be a reading a patient identifier like a barcode, image select, exam start, expose preparatory switch activation, collimation light, and proximity sensor. For example, after positioning the detector 210 the operator can read the barcode on the patient this reading can then be used as a signal that imaging acquisition is desired. For example, the predictor model can be an associative rule like if deactivation has occurred and there is system activity then detector on state 115. Another example is the length of time between activation and deactivation is below a certain threshold to indicate that the image receptor or detector 210 is merely being set down during an interval between two patients. This threshold can be set based on prior experiences. If the predictor recommendation is not to proceed to detector on state 115 then detector is maintained at detector idle state 80. If the predictor determines that the detector should be turned on because imaging is probably then control passes to action 730.

In action 730, the detector is set to the on state. In this state, the detector 210 is set to full power. The action proceeds to action 735 for further processing.

In action 735, a system timeout is determined. The duration of the timeout is based on the system cues received in action 725. There is a range of possibilities that can be specifically tailored to the system cues that form the basis of the predictor in action 725. For example, system cues that are preparatory in nature, such as adjustment of the x-ray technique parameters, result in a longer period. On the other hand, system cues that signal readiness, such as adjustment to system controls, result in a shorter period. The ability to dynamically adjust the period ensures reduction in power consumption and heat generation. If a system timeout is encounter control passes to action 710 where the detector 210 is put in the detector idle state 110. The system timeout 715 is then initialized and checked to see if the detector 210 is to be put into the detector off state 105. If the decision is no then control passes to action 715 where a determination is made as to the status of the activation switch 208. Because the switch 208 is deactivated, control passes to the predictor 725. The function of the predictor 725 is to see if a system cue like an activation of a system control has taken place and an image acquisition event is eminent. If there is no system cue in place, control passes to action 715 to determine if there is a timeout trigger that would cause the detector 210 to be put in the off state. If there is a system cue then the detector is set to an on state and ready for imaging. When a system timeout is not encounter at action 735 control passes to action 740.

In action 740, an image acquisition completion is determined. Action 740 continues until the cycle of imaging is completed, the cycle of imaging can be a single or more images. There are instances were it is desirable to continue to maintain the detector 210 in a power on state because other images need to be acquired from the same patient. Instead of switching between multiple detector states that can add some delays, the detector is maintained in the on state until the cycle of image acquisition is completed. If the image acquisition cycle is completed then control passes to action 745.

In action 745, the detector is placed in the detector off state 70. After the detector is turned off, control passes to the beginning of the process until activation is received. The process by combining operator interaction (705,720) and system interaction (715,725,735,740) is able to automatically manage power consumption and heat generation by the radiography imaging detector 200.

Figure 8:
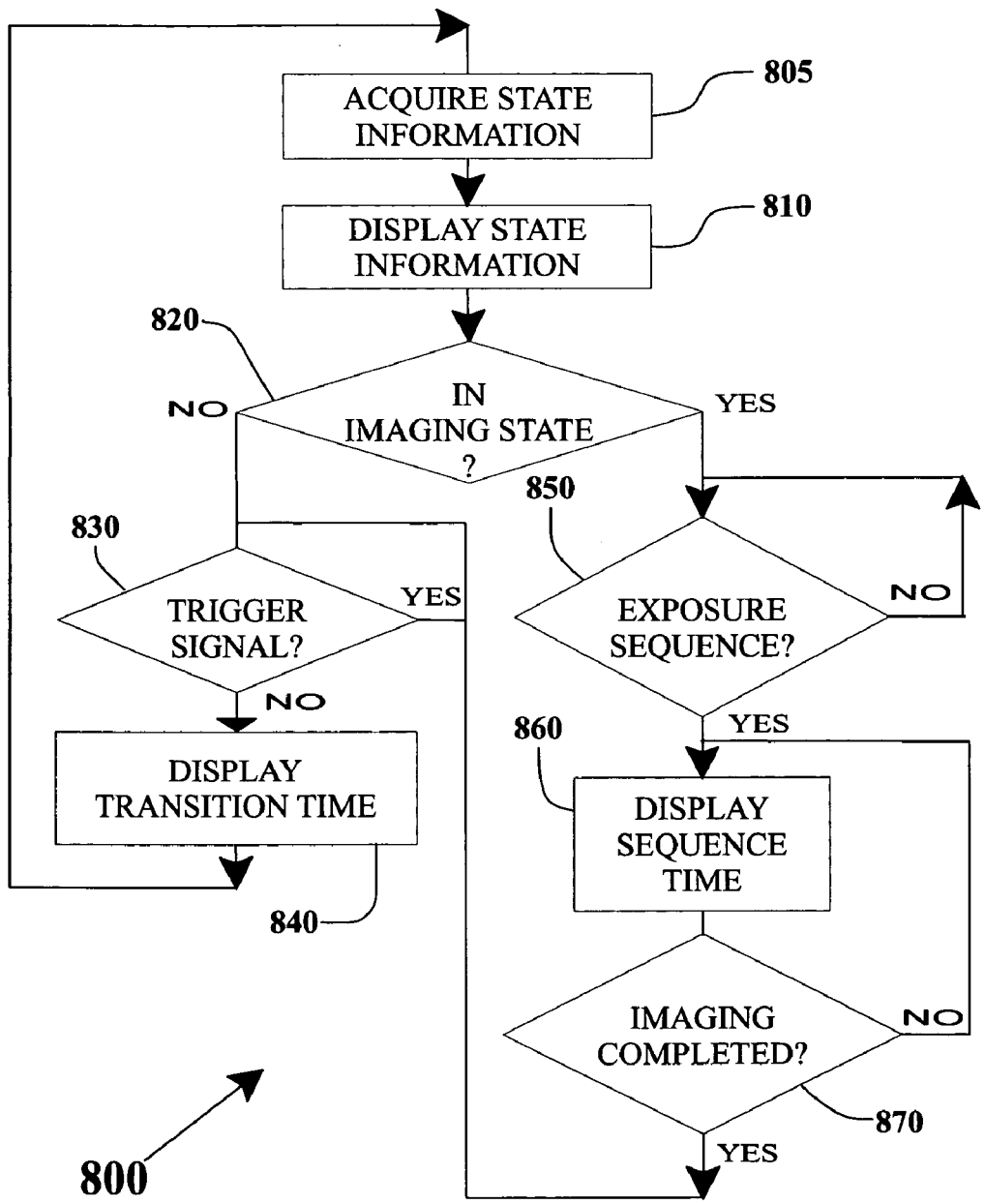
FIG. 8 is a flowchart of a method performed according to an embodiment showing exposure sequence and action of displaying a transition time between states.

FIG. 8 is a flowchart of a method 800 performed by either computer 316, imaging detector controller 314, detector controller 502, operator workstation 322, or by a selective combination of the above according to an embodiment. Method 800 satisfies the need in the art for a reliable, simple and efficient manner to provide a thermal management system with increased power conservation and increased efficiency in a portable battery powered electronic device, and particularly, in a portable battery powered diagnostic medical imaging device.

In action 805, the state of the detector 210 is determined to be one of a detector off state 105, a detector standby state 110, and a detector on state 115. The detector on state 115 is a combination of a ready state and an imaging state. In the ready state, all components necessary to make an x-ray image are powered on and stabilized so that x-ray imaging is possible. The imaging state starts with initiation of an exposure sequence and continues until the sequence is complete. The imaging state is then the imaging acquisition cycle discussed with reference to action 740 of FIG. 7. After the state information is determined, control passes to action 810.

In action 810, the state of the detector is displayed. The display can be any of light emitting diodes (LEDs), liquid crystal display, cathode ray tube (CRT), or any known or later developed display device. After displaying the state of the detector control passes to action 815.

In action 820, an imaging condition is determined. If an imaging condition is determined not to be in effect then control passes to action 830. While a determination is being made as to the imaging state, the detector 210 continues to display the state determined in action 805.

In action 830, a triggering condition is determined as a triggering event. The triggering condition can originate from the system, the activation switch 208, or the reset switch 508. The system trigger can be an activation from the operators, timeouts or interrupts from the system, or any other cue that indicates that a state other than the current state is desired. Further, the operator can simply select the desired state by initiating the reset switch 508. After a triggering condition is detected, control passes to action 840.

In action 840, the transition time is determined and displayed. The transition time is the time required to transition from one state to another. The transition time is dependent upon the number of components that are to be supplied with power. For example, to transition from off to standby requires only that some of the components of the detector 210 are powered-up. Thus, the transition should be relatively short. The transition time can be a value stored at the data repository 320, it could be calculated by the detector based on prior instances, or it could be a running count that stops only when all the necessary components have been powered-up. It is clear that different ways can be envisioned for conveying this information, in the preferred environment a count down is started upon the occurrence of a trigger. After the transition time is determined, control passes to the beginning of the process for a determination of state information 805, and displaying of the state information 810. The process continues until an imaging condition is encountered at action 820. When an imaging condition is determined, control passes to action 850.

In action 850, a determination is made of the exposure sequence. The exposure sequence is one or more image formations that is uniquely defined for a session with the patient or radiated object. The process can only continue to action 860 when the exposure sequence has been identified and defined by the operator.

In action 860, the sequence time is displayed. The sequence time is how long it will take before the detector will again be in the ready state. This time varies with the number of x-ray exposures for the sequence. Control then passes to action 870.

In action 870, imaging completion is determined. The imaging completion is a count of the number of x-ray exposures determined in action 850. If the count has not been satisfied, the process displays the sequence time and starts another x-ray exposure. The process will continue until all the x-ray exposures have been taken for that exposure sequence. Once the exposure sequence has been satisfied, control passes to action 830 for further processing. At action 830, a trigger that is initiated by the operator through the reset switch 508 or by the system. The trigger commands the detector 210 to either go back to the ready state or to go forward to the off state. It should be understood that other states could be possible through a system or reset switch selection. The process permits the operator to be informed of the steps taken by the detector and to acknowledgment that commands are being processed by the system.

Figure 9:
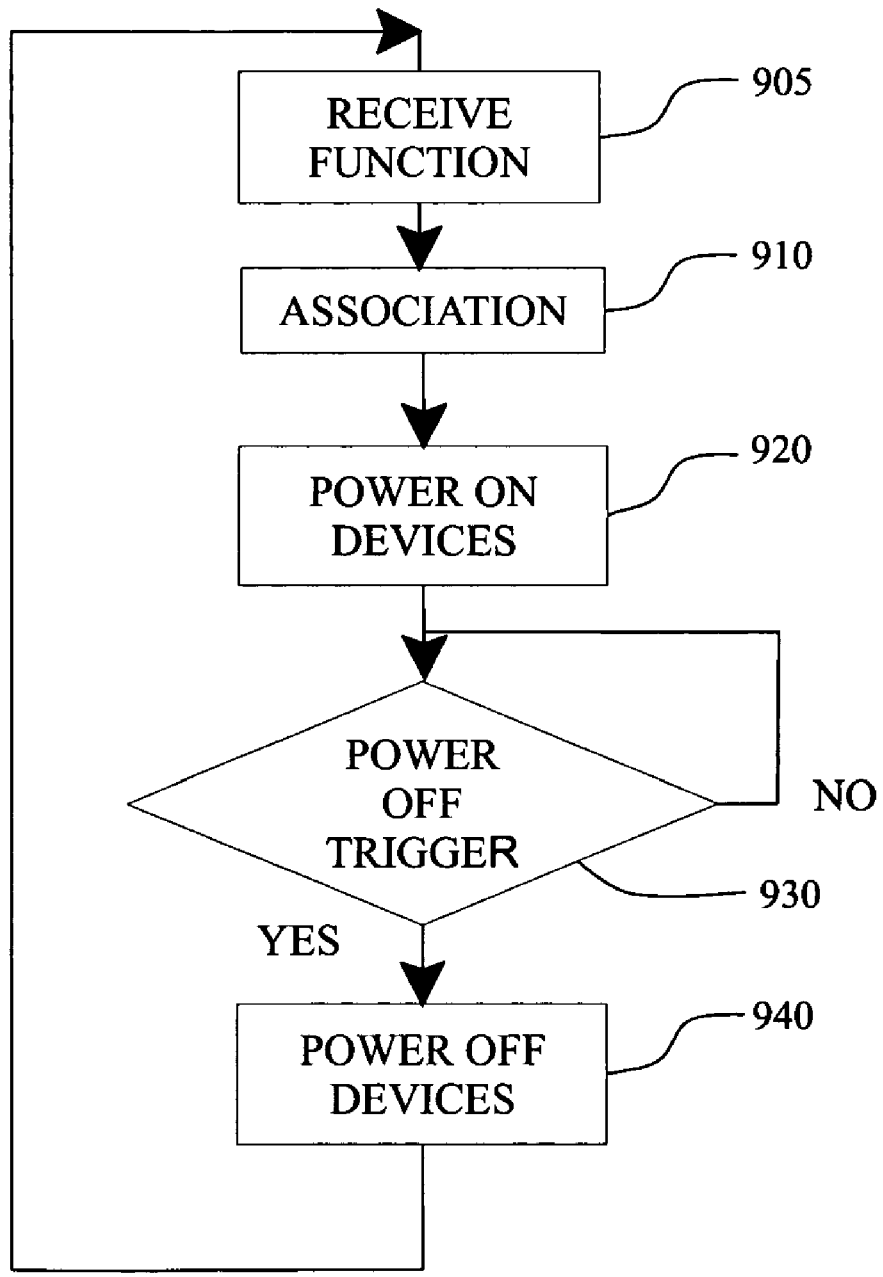
FIG. 9 is a flowchart of a method performed according to an embodiment showing the powering of associated devices for a given function request.

FIG. 9 is a flowchart of a method 900 performed by either computer 316, imaging detector controller 314, detector controller 502, operator workstation 322, or by a selective combination of the above according to an embodiment. The method seeks to manage both the power and temperature of the detector 210 by selectively powering components based on an association of the function with the components needed to perform the function. The selective activation of critical circuits of method 900 satisfies the need in the art for a reliable, simple and efficient manner to provide a thermal management system with increased power conservation and increased efficiency in a portable battery powered electronic device, and particularly, in a portable battery powered diagnostic medical imaging device.

Table II and Table III illustrate the relationship between the function and a trigger; and, between the function and electronics needed to perform the given function. For example, the read sensors function is triggered by a command from the system. The function causes electronic devices such as Panel bias, Row enable (scan), Column enable (data), Transmit/Receive, and Optical power sense to receive power to perform the required function.

TABLE II

Power "ON" and Power "OFF" Function Trigger Association

| Function | Associated Power On Triggers | Associated Power Off Triggers |
| --- | --- | --- |
| Integrate X-ray signal | X-ray prep switch<br>Compression paddle motion | End of readout of x-ray frame<br>End of readout of offset frame<br>Timeout - fixed time without any activity |
| Read pixel array | Command from system | End of readout |
| "Scrub" pixel array | Timeout - fixed time without activity | Timeout - fixed time without activity |
| Read sensors | Command from system | End of reading sensors<br>End of transmitting data |

TABLE II-continued

Power "ON" and Power "OFF" Function Trigger Association

| Function | Associated Power On Triggers | Associated Power Off Triggers |
|---|---|---|
| Perform diagnostics | Command from system | Timeout - fixed time without activity<br>Diagnostic tests complete<br>Diagnostic test data transferred |

TABLE III

Function Electronic Component Association

| Function | Electronics Powered ON | Electronics Powered OFF |
|---|---|---|
| Integrate X-ray signal | Panel bias<br>Row enable (scan)<br>Column enable (data)<br>Transmit/Receive<br>Optical power sense | None |
| Read pixel array | Panel bias<br>Row enable (scan)<br>Column enable (data)<br>Transmit/Receive<br>Optical power sense | None |
| "Scrub1" pixel array (full power/ accurate bias) | Panel bias<br>Row enable (scan)<br>Column enable (data)<br>Transmit/Receive<br>Optical power sense | None |
| "Scrub2" pixel array (lower power/ semi-accurate bias) | Panel bias<br>Row enable<br>Optical power sense | Column enable (data)<br>Transmit/Receive |
| "Scrub3" pixel array (lower power/ accurate bias) | Panel bias<br>Row enable<br>Column enable (data)<br>Optical power sense | Transmit/Receive |
| Read sensors | Control circuitry<br>Sensor circuitry<br>Transmit/Receive<br>Optical power sense | Panel bias<br>Row enable (scan)<br>Column enable (data) |
| Perform diagnostics | Panel bias<br>Row enable (scan)<br>Column enable (data)<br>Transmit/Receive<br>Optical power sense | None |
| Idle | Panel bias<br>Row enable (scan)<br>Optical power sense | Column enable (data)<br>Transmit/Receive |

When a "power on" trigger is detected, the specific trigger and the function requested are determined and electronics that correspond to the function is powered on. One example of electronics that correspond to a function is circuits that are operable to perform that function. Transmit/Receive refers to the detector's ability to receive commands from the X-Ray system or computer 316 via an optical link that, when fully functional, provides high bandwidth at the expense of considerable power consumption. Thus, when it is not needed, powering off most of that functionality will remove most of the link's power consumption. However, if that is the detector's only link to the system, the detector 210 has no other channel to receive commands from the computer 316 once full power is removed from the link, and there will be no means to control the detector 210 to any state except that to which it was last commanded.

The detector 210 is commanded to remove most of the power to the link, and then monitors the optical power from the computer 316 for a transition from the absence of optical power to the presence of optical power. Even with most of the detector's optical link powered off, and complete communication with the system impossible, the detector 210 can sense the state of the optical power coming from the system or computer 316. Therefore, the detector 210 can be commanded by the system to return full power to the optical link, thereby returning full communication capability between the detector and the computer 316. In addition, more than one lower power mode can be supported by any given detector 210. This accommodates holding the power consumed by the detector 210 lower until the time that the function required by the system 316 is needed. For example, if it takes longer to restore accurate bias to the detector 210 than it does to re-establish communication, the detector is commanded to enter the "Scrub3" state after having spent some time in the "Scrub2" state in order to allow time for the detector 210 to accurately restore bias. This could be accomplished by the computer 316 pulsing the optical power to the detector 210, while the detector's transmit and receive functions remain powered off. Then after some period, the computer 316 may restore optical power completely, signaling the detector 210 to perform the same (transition to "Scrub1") in order to reestablish communication in preparation for image acquisition.

In action 905, the request for a given function is received. The request is analyzed and the function is communicated to action 910.

In action 910, a determination is made of the electronics or components that are associated with the requested function. After the association is determined, control passes to action 920.

In action 920 the components associated with the desired function are powered on. Control then passes to action 930 for further processing.

In action 930, a determination is made as to a power off trigger. The power off trigger can be a variety of sources from completing the requested function, system cues like a timeout, operator request from the reset switch 508, or combination of operator and system cues. After a power off trigger is determined, control passes to action 940.

In action 940, the components that were powered on in action 920 are then turned off and control returns to the beginning of further processing. The process permits a quicker stabilization of the detector by predicting based on the desired function which circuits need to be powered on. Further, thermal management is accomplished by a determination of off triggers by the powered on circuit.

Figure 10:
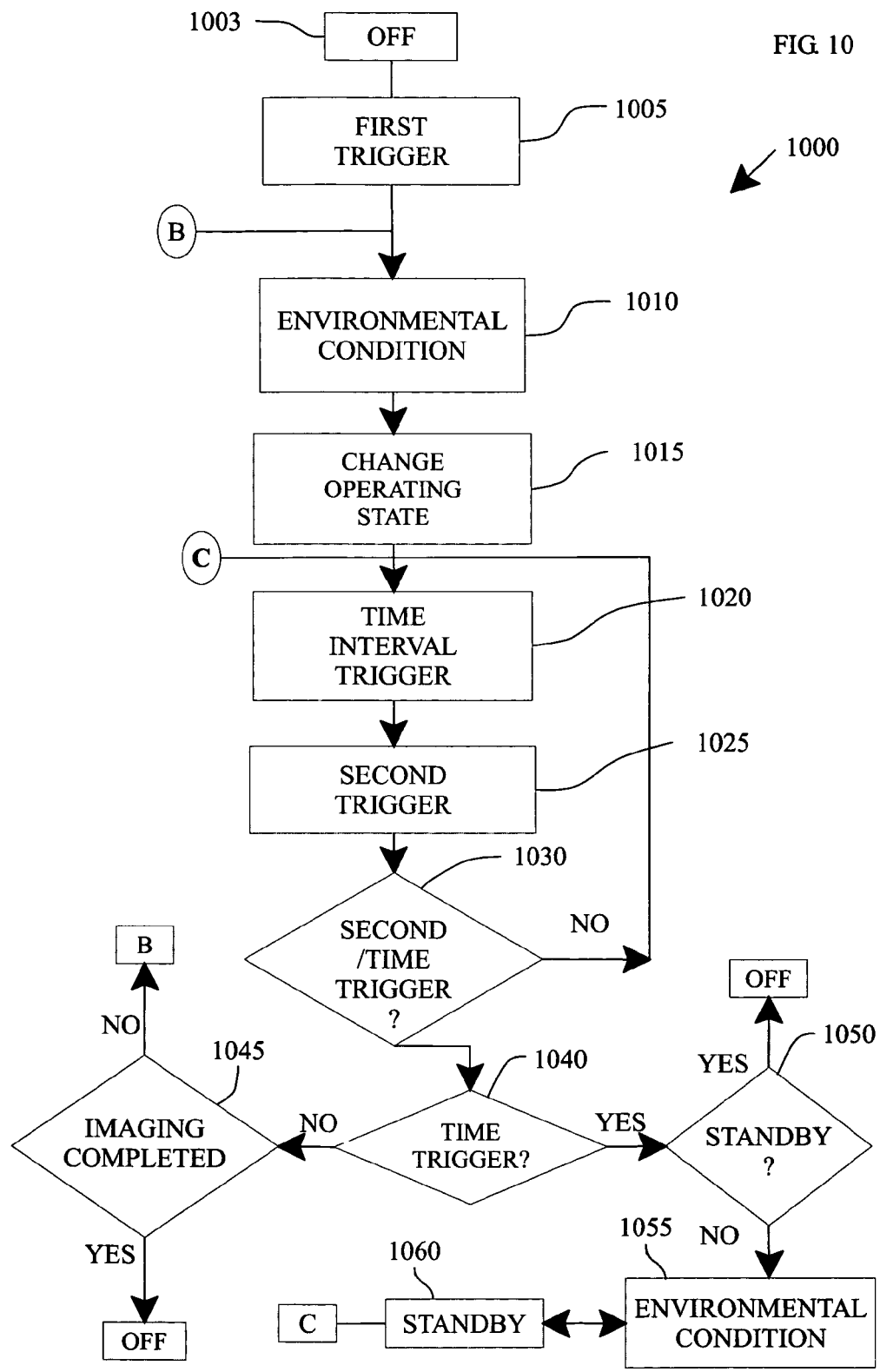
FIG. 10 is a flowchart of a method according to an embodiment the use of environmental conditions and variable time interval for managing the operation of a device.

FIG. 10 is a flowchart of a method 1000 performed by either computer 316, imaging detector controller 314, detector controller 502, operator workstation 322, or by a selective combination of the above according to an embodiment. Method 1000 satisfies the need in the art for a reliable, simple and efficient manner to provide a thermal management system with increased power conservation and increased efficiency in a portable battery powered electronic device, and particularly, in a portable battery powered diagnostic medical imaging device.

In action, 1003 the state of the detector is off. In the off state, a minimal amount of power, usually no power, is provided to the detector. This is the natural state of the detector. After a trigger is received, the process passes to action 1005.

In action 1005, a first triggering signal is received. The genesis of the triggering signal could be from an activation device like activation switch 208, reset signal from reset switch 508, system signal from either computer 316 or workstation 322. The process continues to action 1010.

In action 1010, the environmental condition data is determined. The environmental condition data can be battery status, error status, internal temperature, ambient temperature, diagnostic information, voltage level, or present state of the detector. Once this data is determined, the process continues to action 1015.

In action 1015, the operating state of the detector is changed. The operation state is one of the following: off, standby idle, or on. Each of these states corresponds to different levels of voltage and power consumption, internal temperature, battery capacity or status, and diagnostic status. The internal temperature is proportional to the power consumption. That is, internal temperature increases with an increase in power consumption. Further, a decrease in the power consumption leads to a decrease in internal temperature. After changing the operating state control passes to action 1015.

In action 1015, a time interval trigger is determined. The time interval trigger has as a starting point the occurrence of the first triggering signal. The width of the time interval is dependent upon the environmental conditions. For example if the internal temperature is relatively high and close to an upper level, assuming everything else is equal, an increase in power consumption leads to an increase in internal temperature. In this situation, the duration of the time interval should be shortened due to increase temperature consideration. Additionally, there may be a situation were a higher power consumption is not supported by the detector battery capacity so it is prudent to set the time period as close as possible to zero so as to cause a reversion to a lower power consuming state. The process continues in action 1025.

In action 1025, a second trigger is acquired. The second triggering signal can be a deactivation from the activation switch 208, a signal from the reset switch 508, a system signal or cue that indicates an action by the operator. The second trigger signal can be the combination of other signals to produce a single triggering signal. The process then continues to action 1030.

In action 1030, a determination is made as to whether the second triggering signal or the variable time interval signal has been received. If either of the triggering signals have not been received the process returns to the variable time interval determining action until either of the triggering signals is received. The process then continues to action 1040.

In action 1040, a determination is made as to origin of the triggering signal. If the determination is that a variable time interval signal was the triggering signal then control passes to action 1050.

In action 1050, if the current state of the detector 210 is the standby state then the detector is returned to the off state. If the detector 210 is not in a standby state (on state) then control passes to action 1055. In action 1055, the environmental conditions are read and control passes to action 1060 where the detector's state returns to the standby state and point "C" of the flowchart.

In the event that the triggering signal was a second triggering signal that is indicative of a desire to change the detector's state to an on state. The process continues to action 1045. In action 1045, an imaging completion condition is determined. If the imaging is not completed, then the process continues on to action 1010 for an acquisition of the environmental condition, a changing of the operating state in action 1015, a new variable time interval is determined based on the environmental conditions, and a second time trigger is acquired. Further, when imaging has been completed the detector 210 is taken to the off state until there is another imaging session. In this way, the process solves power and thermal management by monitoring environmental conditions (1010) and altering power consumption based on the environmental conditions.

In some embodiments, methods 700, 800, 900, and 1000 are implemented as a computer data signal embodied in a carrier wave, that represents a sequence of instructions which, when executed by a processor, such as processor 404 in FIG. 4, cause the processor to perform the respective method. In other embodiments, these methods are implemented as a computer-accessible medium having executable instructions capable of directing a processor, such as processor 404 in FIG. 4, to perform the respective method. In varying embodiments, the medium is a magnetic medium, an electronic medium, or an optical medium.

Referring to FIGS. 2-3, particular implementations are described in conjunction with the system overview in FIG. 1 and the methods described in conjunction with FIGS. 7, 8, 9 and 10 that is methods 700, 800, 900 and 1000.

The system indicator, activation, reader, and reset components of the detector 210 can be embodied as computer hardware circuitry or as a computer-readable program, or a combination of both.

More specifically, in the computer-readable program embodiment, the programs can be structured in an object-orientation using an object-oriented language such as Java, Smalltalk or C++, and the programs can be structured in a procedural-orientation using a procedural language such as an assembly language, COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 316 in FIGS. 3 and 4, or on at least as many computers as there are components.

CONCLUSION

A digital radiographic detector has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in medical imaging terms, one of ordinary skill in the art will appreciate that implementations can be made in an industrial or secured environment or any other environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application with respect to is meant to include all object-oriented classes, database objects and communication network environments and alternate technologies which provide the same functionality as described herein.

We claim:

1. A method to manage power consumption of a medical imaging detector comprising:
   receiving a function to be performed by the medical imaging detector;
   determining components of the medical imaging detector that are associated with the received function;
   receiving a first triggering signal based on the components associated with the received function;
   changing the medical imaging detector to a first power consumption state based on the first triggering signal;
   receiving a second triggering signal, wherein the received second triggering signal comprises one of deactivation signal and predictor signal; and
   changing the medical imaging detector to a second power consumption state based on the received second triggering signal.

2. A method of claim 1, wherein the received first triggering signal is an activation signal.

3. A method of claim 1, wherein the first power consumption state is either an off state, an idle state, an on state, the second power consumption state is either an off state, an idle state, an on state.

4. A method of claim 1, wherein the first triggering signal is an activation signal;
   the first power consumption state is an idle state;
   the second power consumption state is either an off state, an on state.

5. A method of claim 1, wherein the received second triggering signal is a system timeout signal.

6. A method of claim 1, wherein the predictor signal is derived from a prediction model.

7. A method of claim 6, wherein the prediction model is based on one or more correlation of pressure data, correlation of force data, probability prediction based time and force of activation, statistic based on prior use, patient identifier indicia reader.

8. A method of claim 1, wherein the received first triggering signal is a deactivation signal,
   wherein the received second triggering signal is an imaging acquisition completed signal.

9. A method of claim 8, wherein the first power consumption state is an on state;
   wherein the second power consumption state is an off state.

10. A method of claim 1, wherein the received second trigger signal is absence of timeout, presence of a deactivation, and presence of a predictor signal.

11. A method of claim 1, wherein the first power consumption state is an on state;
    wherein the second power consumption state is an idle state.

12. A method of claim 11, wherein the received second triggering signal is a system timeout signal.

13. A computer-accessible medium having executable instructions to manage power consumption of a medical imaging detector, the executable instructions capable of directing a processor to perform:
    processing function request to be performed by the medical imaging detector;
    determining components of the medical imaging detector that are associated with the received function request;
    processing a received first triggering signal based on the components associated with the function request;
    changing the medical imaging detector to a first detector power consumption state based on the processed first triggering signal;
    processing a received second triggering signal; and
    changing the medical imaging detector to a second power consumption state based on the processed second triggering signal.

14. The computer-accessible medium of claim 13, wherein the received first triggering signal is an activation signal.

15. The computer-accessible medium of claim 13, wherein the first power consumption state is either an off state, an idle state, an on state; and wherein the second power consumption state is an off state, an idle state, an on state.

16. The computer-accessible medium of claim 13, wherein the received first triggering signal is an activation signal; the first power consumption state is either an off state, an idle state, an on state; and the second power consumption state is either an off state, an idle state, an on state.

17. The computer-accessible medium of claim 13, wherein the received second triggering signal is a system timeout signal.

18. The computer-accessible medium of claim 13, wherein the received second triggering signal is a deactivation signal and predictor signal.

19. The computer-accessible medium of claim 18, wherein the predictor signal is derived from a prediction model.

20. The computer-accessible medium of claim 19, wherein the prediction model is based on one or more correlation of pressure data, correlation of force data, probability prediction based time and force of activation, statistic based on prior use.

21. The computer-accessible medium of claim 13, wherein the received first triggering signal is a deactivation signal; and wherein the received second triggering signal is an imaging acquisition completed signal.

22. The computer-accessible medium of claim 13, wherein the first power consumption state is an on state; and wherein the second power consumption state is an off state.

23. The computer-accessible medium of claim 13, wherein the received second triggering signal is absence of timeout signal, presence of a deactivation signal, and presence of a predictor signal.

24. The computer-accessible medium of claim 13, wherein the first power consumption state is an on state; and wherein the second power consumption state is an idle state.

25. The computer-accessible medium of claim 24, wherein the received second triggering signal is a system timeout signal.

26. A medical imaging system comprising:
    a digital radiographic system having a medical imaging detector;
    processor for processing function request to be performed by the digital radiographic system and for determining components of the digital radiographic system that are associated with the function request;
    a first device for generating a first triggering signal based on the components associated with the function request;
    device for automatically changing the medical imaging detector to a first detector power consumption state based on the first triggering signal;
    a second device for generating a second triggering signal; and
    device for changing the medical imaging detector to a second power consumption state based on the second triggering signal.

27. A medical imaging system of claim 26 further comprising:
    the first device for generating a first triggering signal is an activation switch.

28. A medical imaging system of claim 27 wherein the activation switch further comprises one of an electrical switch, an optical switch, or a capacitive switch.

29. A medical imaging system of claim 28, wherein automatically changing of medical imaging detector to a first power consumption state occurs only if the first triggering signal exceeds an appreciable level.

30. A medical imaging system of claim 29, wherein in the first power consumption state is an idle state; and wherein the second power consumption state is either an off state, or an on state.

31. A medical imaging system of claim 26, wherein the first signal is an activation signal that exceeds an appreciable level;
    wherein the first power consumption state is either an idle state, or an on state; and
    wherein the second power consumption state is either an off state, or an on state.

32. A medical imaging system of claim 26, wherein the second triggering signal is a system timeout signal.

33. A medical imaging system of claim 26, wherein the second signal is a deactivation signal and predictor signal.

34. A medical imaging system of claim 33, wherein the predictor signal is derived from a prediction model.

35. A medical imaging system of claim 34, wherein the prediction model is based on one or more correlation of pressure data, correlation of force data, probability prediction based time and force of activation, statistic based on prior use.

36. A medical imaging system of claim 26, wherein the first trigger signal is a deactivation signal; wherein the second trigger signal is an imaging acquisition completed signal; and the second power consumption state is an off state.

37. A medical imaging system of claim 26, wherein the first trigger signal is a combination of deactivation signal and prediction signal;
    wherein the first power consumption state is an on state; and
    wherein the second power consumption state is an off state.

38. A medical imaging system of claim 26, wherein the first power consumption state is an idle state;
    wherein the second trigger signal is absence of timeout signal, presence of a deactivation signal, and presence of a predictor signal; and
    wherein the second power consumption state is an on state.

39. A medical imaging system of claim 26, wherein the first power consumption state is an on state;
    wherein the second power consumption state is an idle state.

40. A medical imaging system claim 26, wherein the second trigger signal is a system timeout signal.

* * * * *

UNITED STATES PATENT AND TRADEMARK OFFICE
CERTIFICATE OF CORRECTION

PATENT NO. : 7,409,564 B2  Page 1 of 1
APPLICATION NO. : 10/805753
DATED : August 5, 2008
INVENTOR(S) : Ken Kump et al.

It is certified that error appears in the above-identified patent and that said Letters Patent is hereby corrected as shown below:

Col. 24, Line 44
Please replace claim 1 with the following:

40. A medical imaging system of claim 26, wherein the second trigger signal is a system timeout signal.

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,409,564 B2  
APPLICATION NO. : 10/805753  
DATED : August 5, 2008  
INVENTOR(S) : Ken Kump et al.

Page 1 of 1

It is certified that error appears in the above-identified patent and that said Letters Patent is hereby corrected as shown below:

Col. 24, Line 44  
Please replace claim 40 with the following:

40. A medical imaging system of claim 26, wherein the second trigger signal is a system timeout signal.

This certificate supersedes the Certificate of Correction issued December 23, 2008.

Signed and Sealed this

Twenty-seventh Day of January, 2009

JOHN DOLL  
*Acting Director of the United States Patent and Trademark Office*